United States Patent [19]

Kuroda et al.

[11] Patent Number: 6,132,743
[45] Date of Patent: Oct. 17, 2000

[54] ZINC OXIDE POWDER WITH SUPPRESSED ACTIVITY AND COSMETIC PREPARATION

[75] Inventors: Akihiro Kuroda, Odawara; Yoshinori Waki; Masataka Shimomura, both of Osaka, all of Japan

[73] Assignees: Kanebo, Ltd., Tokyo; Daito Kasei Kogyo Co., Ltd., Osaka, both of Japan

[21] Appl. No.: 09/284,933

[22] PCT Filed: Oct. 23, 1997

[86] PCT No.: PCT/JP97/03841

§ 371 Date: Jul. 6, 1999

§ 102(e) Date: Jul. 6, 1999

[87] PCT Pub. No.: WO98/17730

PCT Pub. Date: Apr. 30, 1998

[30] Foreign Application Priority Data

Oct. 23, 1996 [JP] Japan ..................... 8-299658
Oct. 23, 1996 [JP] Japan ..................... 8-299659

[51] Int. Cl.[7] .............. A61K 7/00; A61K 7/42; A61K 9/14; C04B 14/00; C01G 9/02

[52] U.S. Cl. .......................... 424/401; 106/425; 106/426; 106/429; 423/622; 424/59; 424/489; 424/642

[58] Field of Search ...................... 424/401, 489, 424/59, 642; 423/622; 106/425, 429, 426

[56] References Cited

U.S. PATENT DOCUMENTS 5,366,660 11/1994 Tapley .......................... 252/309
5,536,492 7/1996 Mitchnick et al. ................ 424/59

FOREIGN PATENT DOCUMENTS 06009898 1/1994 Japan .
6-80421 3/1994 Japan .

*Primary Examiner*—Shelley A. Dodson
*Assistant Examiner*—Marina Lamm
*Attorney, Agent, or Firm*—Flynn, Thiel, Boutell & Tanis, P.C.

[57] ABSTRACT

A zinc oxide powder having a suppressed photocatalytic activity and prepared by coating a zinc oxide powder with at least one silicone compound in a nongaseous state and firing the coated zinc oxide powder in an oxidizing atmosphere at a temperature of 600 to 950° C. A cosmetic preparation containing this zinc oxide powder is excellent in feel, sebum resistance, and protection against ultraviolet light.

14 Claims, No Drawings

ZINC OXIDE POWDER WITH SUPPRESSED ACTIVITY AND COSMETIC PREPARATION

TECHNICAL FIELD

The present invention relates to a zinc oxide powder having an excellent feel, sebum resistance and protection against ultraviolet rays in which a photocatalytic activity is suppressed by coating powdery zinc oxide with silicon oxide. The invention also relates to a cosmetic compounded preparation thereof.

More specifically, the present invention relates to a zinc oxide powder having an excellent feel, sebum resistance and protection against ultraviolet rays in which a photocatalytic activity is suppressed through the formation of silicon oxide on the surface of powdery zinc oxide by surface-coating the powdery zinc oxide with at least one silicone compound such as an organo polysiloxane and a silicone resin, and firing the resulting powder at a high temperature. The invention also relates to a cosmetic compounded preparation thereof.

BACKGROUND ART

Zinc oxide powder has been formerly frequently used in cosmetic preparations, etc. as an extender pigment or for cutting light in the UV-A region. However, since the zinc oxide powder absorbs the ultraviolet light by cleaving zinc-oxide bonds, it has a problem in that the amount of radicals generated is large among powders used in the cosmetics. For this reason, it is troublesome in compounding zinc oxide powder that the compounding amount of the zinc oxide powder and other compounded ingredients coexistent with the powder must be severely selected due to the photocatalytic activity of the zinc oxide powder. In order to suppress the photocatalytic activity of the zinc oxide powder, its surface needs to be coated with a material having a low activity, and particularly is preferably coated with an inorganic oxide. For example, there are conventional inorganic oxide-coating methods as follows. ① As proposed in JP-A-3 183,620, etc., silicon oxide or the like is precipitated and coated upon the surface of the zinc oxide fine powder by controlling the pH in a wet state so that the solid acidic catalytic activity of the zinc oxide fine powder maybe suppressed and the coefficient of dynamic friction may be reduced. ② As proposed in JP-A 63- 139,015, particularly in order to reduce the aggregation of a powder, a vapor of a cyclic silicone compound, or that of a straight-chain silicone compound having a low molecular weight is brought into contact with active sites of the powder, the silicone compound is polymerized by the active sites of the powder, and then the resulting polymer is fired. ③ As proposed in JP-A 8-59,238, in order to suppress the photocatalytic activity of the zinc oxide powder and improve its dispersibility, the surface of the zinc oxide powder is treated with an aluminum chelate compound and a silane compound, and the thus treated zinc oxide is coated with aluminum oxide and silicon oxide after being fired at 500° C. ④ As proposed in JP-A 6-80,421, in order to obtain scaly zinc oxide flake powder having an excellent ultraviolet light shielding effect and mechanical strength, the scaly zinc oxide is precipitated in a wet state under coexistence with aluminum sulfate or the like, and then the resulting precipitant is fired at 850 to about 1,000° C.

In the above methods ① and ④, zinc oxide is dissolved in a weak acid or a weak alkali because zinc oxide is an amphoteric substance, so that zinc ions are re-precipitated upon the surface of the powder during the controlling of the pH even after a treatment. Consequently, there are problems in that the photocatalytic activity cannot be sufficiently suppressed or the powder is strongly aggregated. On the other hand, according to the above method ②, the silicon compound must be once fed, in the form of a vapor, to the powder, so that the method is troublesome and time-consuming, the amount of the treating silicone compound depends upon the catalytic activity of the powder to disable the free control of the treating amount, and the feel of the resultant powder becomes harder. According to the above method ③, since the amount of the metal is small for the large molecular weight of the aluminum chelate compound and the large molecular weight of the silane compound, the reaction needs to be assuredly effected during the coating treatment, while a byproduct needs to be removed. Further, when the zinc oxide is simply coated with the aluminum chelate compound or the silane compound and the resultant is fired, the fired coating oxide film becomes porous, so that the photocatalytic activity cannot be sufficiently suppressed.

In view of the above-mentioned problems, the present inventors strenuously examined the coating condition, the heating temperature condition, etc. for the zinc oxide powder, and consequently discovered that by surface-coating powdery zinc oxide with at least one silicone compound selected from an organo polysiloxane and a silicone resin in a non-gaseous phase, and firing the resulting powder at a temperature of 600 to 950° C., the photocatalytic activity of the zinc oxide powder can be more easily suppressed, and the modified powder having an excellent feel can be more easily obtained.

Further, the inventors discovered that a cosmetic preparation containing this activity-suppressed zinc oxide powder is excellent in product stability, feel, sebum resistance, and protection against ultraviolet light.

DISCLOSURE OF THE INVENTION

That is, a first invention relates to an activity-suppressed zinc oxide powder coated with silicon oxide, said activity-suppressed zinc oxide powder being obtained by coating powdery zinc oxide with at least one silicone compound selected from an organo polysiloxane and a silicone resin in a nongaseous phase, and firing the resulting powder at a temperature of 600 to 950° C. in an oxygen-containing atmosphere.

The average primary particle diameter of the powdery zinc oxide used in the present invention is in a range of 5 nm to 20 $\mu$m, more preferably in a range of 10 nm to 300 $\mu$m.

The coated amount of the silicone compound in the activity-suppressed zinc oxide powder according to the present invention is preferably 2 to 80 wt %, more preferably 2 to 9 wt %, of the total weight of the powdery zinc oxide and the silicone compound.

With respect to the photocatalytic activity of the activity-suppressed type zinc oxide powder according to the present invention, the generating intensity angles of super oxide anion radicals immediately after the start of light irradiation is not more than 4 degrees.

The activity-suppressed type zinc oxide powder according to the present invention, which is coated and fired, has the feature, as compared with a zinc oxide powder obtained by firing a non-coated powdery zinc oxide at said temperature, a half-value width of a peak peculiar to a (100) plane and a (010) plane and a half-value width of a peak peculiar to a (101) plane and a (011) plane in X-ray diffraction given from a wurtzier type crystalline structure of zinc oxide are larger, and the half-value width of the peak peculiar to each of the crystalline planes takes the following value depending upon a crystallinity of the powdery zinc oxide not coated or fired as a starting material as calculated by a density method: the half-value widths of the peaks in the (100) and (010) planes and (101) and (011) planes, respectively, are in a range of 0.25±0.10, and differences among them being not more than 0.02, if the crystallinity of the powdery zinc oxide as a starting material is not less than 0.7; or said half-value widths are in a range of 0.50±0.10, and differences among them being not more than 0.02, if the crystallinity of the powdery zinc oxide as a starting material is less than 0.7.

A second invention is directed to a cosmetic preparation containing the activity-suppressed type zinc oxide powder obtained by the first invention.

The cosmetic preparation preferably contains the above activity-suppressed type zinc oxide powder and at least one ultraviolet light-shielding ingredient.

The cosmetic preparation according to the present invention preferably contains the above activity-suppressed type zinc oxide powder and at least one antioxidant.

BEST MODES FOR WORKING THE INVENTION

In the following, working embodiments of the present invention will be explained in more detail.

The average primary particle diameter of the powdery zinc oxide to be used in the present invention is preferably in a range of 5 nm to 20 µm, more preferably in a range of 10 to 300 nm. If the average primary particle diameter is less than 5 nm, the powdery zinc oxide can be hardly industrially obtained due to the too small particle diameter. If the average primary particle diameter is more than 20 µm, the powdery zinc oxide has poorer functional characteristics due to the too large particle diameter. In the case of a fine powdery zinc oxide having a primary particle diameter in the range of 10 to 300 nm, the powder itself has a strong activity, so that the merit of reducing the activity of the powder by the surface treatment can be most realized.

The powdery shape of the zinc oxide to be used in the present invention may include "spherical", "planar", "spindle", "amorphous" and "rod", but is not particularly limited.

The powdery zinc oxide to be used in the present invention is purely expressed by a chemical formula, ZnO, which includes a compound belonging to the hexagonal system and forming a wurtzite type crystalline structure as well as powders surface-coated with zinc oxide, such as titanium oxide treated with zinc oxide and mica coated with zinc oxide.

The silicone compound to be used in the present invention includes silicone compounds, excluding silane compounds, having at least five silicon atoms, for example, organo polysiloxanes such as methylhydrogenpolysiloxane, dimethylpolysiloxane, methylphenyl polysiloxane, biphenylpolysiloxane, alkyl-modified silicone, and alkoxy-modified silicone, silicone resins such as trimethylsiloxy silicate, acrylsilicone and silicone RTV rubber. The organosiloxane, the silicone resin, a silane coupling agent, an aluminum coupling agent and a silicone having three to four silicon atoms may be simultaneously used. The above silicone compound is a liquid or solid at ordinary temperatures. The solid silicone resin may be used in the state that it is dissolved in a solvent. The silicone compound is particularly preferably methylhydrogenpolysiloxane and methylpolysiloxane. Further, silicone compounds having 8 to 100 silicon atoms are preferred because such have excellent uniform treating power.

The coating treatment employed in the present invention needs to be effected in the non-gaseous phase state so as to attain a coating degree sufficient to suppress the photocatalytic activity of the powdery zinc oxide. The non-gaseous phase state means that the powdery zinc oxide is contacted and coated with at least one silicone compound in the state that the silicone compound and zinc oxide are liquid/solid or solid/solid. As the coating method, the following may be recited.

① Wet method: The powdery zinc oxide is coated by mixing, stirring and dispersing the zinc oxide and at least one silicone compound with the use of a solvent such as an alcohol, toluene, water or a volatile silicone, and removing the solvent.

② Dry method: The powdery zinc oxide is coated with at least one silicone compound by using a mixing device such as a mixer.

③ Mechanochemical method: The powdery zinc oxide is mechanically coated with at least one silicone compound by using a device such as a ball mill.

In the above methods, it may be that the powder is finely milled by using a bead mill or the like, and/or that the coated powder is preliminarily heated up to around 200° C. The preheating treatment is preferable, because a fire catching problem can be avoided in the evaporation of an ingredient with a low boiling point during the succeeding firing step. Further, two or more silicon compounds recited above maybe used together. A compound containing fluorine or chlorine is not preferred for the coating because such a compound generates a fluorine gas or a chlorine gas during the succeeding firing step, which damages the firing device.

The coating amount of the silicone compound for the powdery zinc oxide according to the present invention is preferably 2 to 80 wt %, more preferably 2 to 9 wt % relative to the entire weight of the powdery zinc oxide and the silicone compound. Such a range of the coating amount exhibits excellent photocatalystic activity-suppressing effect, feel, sebum resistance and ultraviolet light-shielding effect. The range of 2 to 80 wt % can give a peculiar smooth feel to the powder. This feel cannot be obtain if the same amount of silica is wet treated or surface-treated in a gaseous phase state. The range of 2 to 9 wt % is a range in which almost no aggregation occurs by firing, and excellent photocatalystic activity-suppressing effect, feel, sebum resistance and ultraviolet light-shielding effect can be fully exhibited without post grinding the powder.

According to the present invention, after the above coating treatment, the firing treatment is effected in air, oxygen or a mixture of oxygen and other gas as an oxygen-containing atmosphere in a temperature range of preferably 600 to 950° C., more preferably 700 to 900° C., and most preferably 750 to 850° C. If the temperature is less than 600° C., a film of silicon oxide is hardly formed, and the photocatalytic activity is not sufficiently suppressed. If the temperature is more than 950° C., the zinc oxide powder may aggregate, so that the ultraviolet light-shielding effect is reduced and feel is damaged. In particular, if the temperature is 1,700° C. or more, zinc oxide is sublimated as a poisonous gas. If the powder is fired in a temperature range of 600 to 950° C., the problems regarding sublimated gas generation, cost-up, stability, activity sealingness, etc. can be solved. The firing time differs depending upon the firing temperature, the coating compound used, etc. For example, it may be 1 minute to 2 days, but not restricted thereto. In general, the time period of 0.5 to 12 hours is industrially preferred, and particularly the firing time period (excluding the temperature-rising time period and the cooling time period) at a set temperature is preferably 2 to 6 hours. According to the invention method, since various decomposed products occur from the silicone compound during the firing step, the firing device is provided with exhaust gas-treating equipment.

If the heating temperature is low and the primary particle diameters of the powdery zinc oxide are small, a small amount of silicon oxide is formed in some cases on the surface of the powder besides silicon oxide. Since such cases conform with the invention object of suppressing the activity, no large problem occurs.

The activity-suppressed zinc oxide powder according to the present invention is featured by the crystalline structure and the photocatalytic activity. The crystalline lattice of zinc oxide in the activity-suppressed zinc oxide powder according to the present invention is preferably relatively small from the standpoint of the crystalline structure. That is, as compared with a zinc oxide powder obtained by firing a non-coated powdery zinc oxide at said temperature, a half-value width of a peak peculiar to a (100) plane and a (010) plane and a half-value width of a peak peculiar to a (101) plane and a (011) plane in X-ray diffraction given from the wurtzite type structure of zinc oxide are larger if the powdery zinc oxide, which belongs to the hexagoanl system and forms the wurtzite type crystalline structure, is coated with the silicone compound, followed by firing, and the half-value width of the peak peculiar to each of the crystalline planes takes the following value depending upon the crystallinity of the non-coated and non-fired powdery zinc oxide as a starting material as calculated by a density method. That is, the half-value widths of the peaks in the (100) and (010) planes and (101) and (011) planes, respectively, are in a range of 0.25±0.10, and differences among them being not more than 0.02, if the crystallinity of the powdery zinc oxide as a starting material is not less than 0.7; or said half-value widths are in a range of 0.50±0.10, and differences among them being not more than 0.02, if the crystallinity of the powdery zinc oxide as a starting material is less than 0.7.

The activity-suppressed zinc oxide having an excellent photocatalytic activity-suppressing effect can be obtained if the half-value widths take the above values.

The X-ray diffraction measurement and the crystallinity-measurement on the density method are as follows.

(X-ray diffraction measurement)
Measuring apparatus: RINT-1100 type manufactured by Rigaku Co., Ltd.
X-ray tube: Cu tube
Tube voltage: 30 kV
Tube current: 10 mA
X-ray incidence angle: 2θ=2° to 60°
Sample measured: A sample was uniformly filled on an aluminum plate having dimensions of 20×18 mm.
Measured peak: Half-value widths at 2θ=31.8° and 2θ=36.3° was employed.
Plane distance: Bragg's expression: λ=2d sinθ in which d is a distance between lattice planes, θ is a Bragg's angle and λ is a wavelength of X-rays used.

It is seen that d=2.808 Å was calculated at 2θ=31.8°, which corresponds to a distance between the (100) plane and the (010) plane, and 2θ=36.3° corresponds to that between the (101) plane and the (011) plane according to the distance between reverse lattice planes of the crystalline lattice of the wurtzite type structure.

(Measurement of the crystallinity degree)

$$S=ScX+Sam(1-X) \quad (1)$$

in which X is a crystallinity degree, S is a specific gravity, Sc is the specific gravity of the crystal (5.47 in zinc oxide) and Sam is the specific gravity of an amorphous material (5.78 in zinc oxide).

The crystallinity can be determined from the formula (1) if the specific gravities are available. The specific gravities are determined by the following formula.

$$S(t/4° C.)=[(W_2-W_1)(S_1-S_a)]/[(W_4-W_1-(W_3-W_2)]+Sa$$

in which
$W_1$: a figure obtained by weighing the specific gravity bottle in air.
$W_2$: a figure obtained by weighing the specific gravity bottle containing a sample in air.
$W_3$: a figure obtained by weighing the specific gravity bottle containing a sample and a liquid at t° C. in air.
$W_4$: a figure obtained by weighing the specific gravity bottle containing the liquid at t° C. in air.
$S_1$: the specific gravity of the liquid at t° C. in air
$S_a$: the specific gravity of air, i.e., 0.012, provided that it may be ignored if the necessary precision of the specific gravity is two digits.

In the present invention, the photocatalytic activity was evaluated by using the following evaluating method, and a radical-generating intensity angle is preferably not more than 4 degrees. If the radical-generating intensity angle is preferably not more than 4 degrees, the photocatalytic activity is suppressed. The radical-generating intensity angle of a commercially available non-treated zinc oxide powder was measured to be in a range of 12 to 30 degrees.

(Evaluating method for the photocatalytic activity)
A sample is dispersed into a 90 wt % ethanol aqueous solution by using ultrasonic waves, thereby producing a 0.05 wt % sample solution. A radical-trapping agent is added into the sample solution, and the resultant composition is mixed by using ultrasonic waves. As a ultraviolet irradiating source, a Xenon lamp, a D2 lamp, a high pressure mercury lamp or the like is used, and ultraviolet rays in a visible light, infrared light and UV-C regions are filtered to irradiate ultraviolet rays in the UV-A and UV-B regions. The ultraviolet rays are irradiated upon a sample container placed in an ESR by using an optical fiber. The amount of super oxide anion radicals, as a target, generated for a time period of 0 to 750 seconds from the irradiation was measured by the ESR (OH-radicals and methyl radicals are present as kinds of radicals, but the super oxide anion radicals are preferred from the standpoint of measuring the photocatalytic activity of the zinc oxide powder itself). The measured values of the samples were compared by using relative values while a value of Mn measured at the same time was taken as 100 so as to correct errors among them.

Since a clear theory has not been established to date for the evaluation of the activity, either one of the following two ways of evaluations has been used. Herein, evaluations were effected by using the radical-generating intensity angles. The maximum amount of the radicals generated may be used, and it can be recognized that the radical-generated amount is reduced by the surface treatment. However, this has a problem in that a correlationship between the maximum amount and the photocatalytic activity is still unclear.

(A) Rising angles of peaks from 0 second after the irradiation (Radical-generating intensity angles) are compared.

(B) Maximum amount of radicals generated in a time period of 0 second to 750 second after the irradiation are compared.

The measurement results of samples which have a poor stability in a dispersion liquid and rapidly precipitates, are omitted from the evaluations as having no quantitative values.

(Measurement of radical-generating intensity angles)

The gradient of a graph (the inclination of a tangent) at an initial stage of the radical generation is determined from the graph of the radical-generating amount immediately after the irradiation (for 0 to a few minutes). The inclination "k" is expressed by k=radical-generated amount (relative amount of manganese)/time period (unit: second). The radical-generating intensity angle "r" has the following relationship to "k", which enables the determination of the angle.

$$r \text{ (unit: degree)} = \tan^{-1}(k)$$

For example, assuming that a tangent passes through the origin and a position (37 seconds, Mn relative value 10), $r = \tan^{-1}(10/37) = 15$ degrees.

According to the present invention, the activity-suppressed zinc oxide powder obtained may be used after being subjected to a conventional known surface treatment such as a silicone treatment, a silane treatment, a fluorine compound treatment, an oily treatment, a metallic soap treatment, a wax treatment, an N-acylated lysine treatment, a metal oxide treatment, a methylmethacrylate resin treatment, a tackifier treatment, a plasma treatment or a mechanochemical treatment.

The activity-suppressed zinc oxide powder according to the present invention may be applied to resins, paints, inks, glasses, fibers, papers, etc. besides cosmetic preparations.

The cosmetic preparation which belongs to the second invention exhibit more excellent ultraviolet light-shielding effects by using the activity-suppressed zinc oxide powder and at least one kind of ultraviolet light-shielding component in combination. As the ultraviolet light-shielding component, organic and inorganic ultraviolet light-shielding components which correspond to UV-A (wavelength: 400 to 320 nm) and UV-B (wavelength: 320 to 280 nm) may be used. As examples of the organic ultraviolet light-shielding component, for example, mention may be made of paramethoxy cinnamic acid 2-ethylhexyl, paradimethyl aminobenzoic acid2-ethylhexyl, 2-hydroxy-4-methoxy-benzophenone, 2-hydroxy-4-methoxybenzophenone-5-sulfuric acid, 2,2'-dihydroxy-4-methoxybenzophenone, p-methhoxy hydrocinnamic acid diethanol amine salt, paraaminobenzoic acid (hereinafter abbreviated as "PABA"), homomentyl salicylate methyl-O-aminobenzoate, 2-ethylhexyl-2-cyano-3,3-diphenylacrylate, octyldimethyl PABA, octyl methoxycinnamate, octyl salicylate, 2-phenyl-benzimidazol-5-sulfuric acid, salicylic acid triethanolamine, 3-(4-methylbenzylidene)camphor, 2,4-dihydroxybenzophenone, 2,2',4,4'-tetrahydroxybenzophenone, 2,2'-dihydroxy-4,4'-dimethoxy-4,4'-dimethoxybenzophenone, 2-hydroxy-4-N-octoxybenzophenone, 4-isopropyldibenzoylmethane, butylmethoxydibenzoylmethane, 4-(3,4-dimethoxyphenylmethylene)-2,5-dioxo-1-imidazolidine propionic acid 2-ethylhexyl, a triazine derivative, shea butter, pongamia extract and polymer derivatives thereof.

As the inorganic ultraviolet light-shielding component, mention may be made of titanium dioxide, lower oxide-content titanium oxide, cerium oxide, cobalt oxide, cerium-zirconium oxide, iron-doped titanium oxide, etc., which have an average primary particle diameter in a range of 5 to 300 nm. The powdery shape thereof may be spherical, spindle, rod-like, amorphous or the like, but not particularly restrictive. The powder may be subjected to a conventional known surface treatment. As examples of the surface treatment mention may be made of conventional known surface treatments such as a silicone treatment, a silane treatment, a fluorine compound treatment, an oily treatment, a metallic soap treatment, a wax treatment, an N-acylated lysine treatment, a metal oxide treatment, a plasma treatment, a mechanochemical treatment and a tackifier treatment.

It is preferable to also use an antioxidant in the cosmetic preparation according to the present invention from the standpoint of preventing a change in the quality of other compounded ingredients by the photocatalytic activity of the zinc oxide powder, etc. As examples of the antioxidant, mention may be made of conventionally known materials, for example, antioxidants originating from plants, etc., such as tocopherols, SOD, phenols, terpenes, butylhydroxytoluene, vitamin C, vitamine E, catechins, glucose, hyaluronic acid, β-carotene, tetrahydrocurcumin, tea extract, sesame extract, anthocyanin, glycoside, etc.

The cosmetic preparation according to the present invention, ingredients commonly used in cosmetic preparations, such as an oily agent, powders (pigment, colorant, resin), a fluorine compound, a resin, a surface active agent, a tackifier, an antiseptic, a perfume, a humectant, a physiologically active ingredient, a salt, a solvent, a chelating agent, a neutralizing agent, a pH adjuster, etc. may be simultaneously compounded.

As the powders, mention may be made of colorants such as D&C Red No. 28 (C.I. No. 45410), D&C Red No. 6 (C.I. No. 15850), FD&C Yellow No. 5 (C.I. No. 14140), FD&C Blue No. 1 (C.I. No. 42090) Acid Black 1 (C.I. No. 20470), lake colorants such as FD&C Yellow No. 5 (C.I. No. 19140) A1 lake and D&C Yellow No. 10 (C.I. No. 47005) Ba lake, polymers such as nylon powder, silk powder, urethane powder, polyfluoroethylene powder, silicone powder, cellulose powder and silicone elastomer, color pigments such as yellow iron oxide, red iron oxide, black iron oxide, chromium oxide, carbon black, ultramarine and Prussian blue, fillers such as talc, mica, sericite and kaolin, pearl pigments such as mica titanium, metal salts such as barium sulfate, calcium carbonate, magnesium carbonate, aluminum silicate and magnesium silicate, inorganic powders such as silica and alumina, titanium oxide fine powder, iron oxide fine powder, alumina-treated iron oxide fine powder, silica-treated titanium oxide fine powder, bentonite and smectite. With respect to these powders, no particular limitations are posed upon the shape and the size. These powders may be subjected to conventional surface treatment such as the silicone treatment and fluorine compound treatment as mentioned above.

As the oily agent, mention may be made of higher alcohol such as cetyl alcohol, isostearyl alcohol, lauryl alcohol, hexadecyl alcohol, and octyldodecanol, fatty acids such as isostearic acid, undecylenic acid and oleic acid, polyhydric alcohols such as glycerol, sorbitol, ethylene glycol, propylene glycol and polyethylene glycol, esters such as myristyl myristylate, hexyl laurylate, decyl oleate, isopropyl mirystylate, hexyldecyl dimethyloctanoate, monostearic acid glycerol, dimethyl phthalate, monostearic acid ethylene glycol and octyl oxystearate, hydrocarbons such as liquid paraffin, vaseline and squalane, waxes such as lanolin, reduced lanolin and carnauba wax, oils and fats such as mink oil, cacao butter, coconut oil, palm kernel oil, tsubaki oil, sesame oil, caster oil and olive oil, ethylene•α-olefin•oligomer, etc.

As other oily agents, for example, mention may be made of silicone compounds such as dimethylpolysiloxane, methylhydrogen polysiloxane, methylphenyl polysiloxane, polyether-modified organopolysiloxane, fluoroalkyl•polyoxyalkylene-modified organopolysiloxane, alkyl-modified organopolysiloxane, terminal-modified organopolysiloxane, fluorine-modified organopolysiloxane, Amodimethicone, amino-modified organopolysiloxane, silicone gel, acryl silicone, trimethylsiloxysilicate acid and silicone RTV rubber, fluorine compounds such as perfluoropolyether, fluorinated pitch, fluorocarbons, fluoroalcohols and fluorinated silicone resins, etc.

As the surface active agent, for example, mention may be made of an anionic surface active agent, a cationic surface active agent, a nonionic surface active agent and a betaine surface active agent.

As the solvent, mention may be made of purified water, ethanol, soft liquid paraffin, a lower alcohol, ethers, LPG, fluorocarbons, N-methylpyrrolidone, fluoroalcohols, perfluoropolyethers, substituting Flon and volalite silicone.

As the cosmetic preparation according to the present invention, mention may be made of make-up cosmetic foundations, such as foundations, white powders, eye shadows, eye liners, cheeks, lip sticks, and nail colors, fundamental cosmetic preparations such as milky lotions, creams, lotions, calamine lotions, sun screen agents, suntan agents, after-shave lotions, pre-shave lotions, pack preparations, cleansing preparations, facial cleansing preparations and acne preventing cosmetic preparations, hair colors, body powders, deodorants, soaps, body shampoos, bathing preparations, perfumes, etc.

In the cosmetic preparation according to the present invention, the compounding amount of the activity-suppressed zinc oxide powder is preferably 0.1 to 100 wt %, more preferably 1 to 60 wt % relative to the total weight of the cosmetic preparation. The compounding amount of the ultraviolet light shielding component is preferably 0.1 to 50 wt %, and that of the antioxidant is 0.001 to 10 wt %.

As types of the cosmetic preparations according to the present invention, use may be made of conventionally known types such as two-layered types, oil-in water emulsions, water-in oily emulsions, gel types, spray types, mousses, oily types and solid types. As uses for the sun screen preparations, the two-layered type, the oil-in water emulsion and the gel type are preferred. As uses for the foundations, the solid-emulsion type, the gel type, the oil-in water emulsion, the water-in oil emulsion, the oil type, mousses, etc. are preferred.

EXAMPLES

In the following, the present invention will be explained in more detail based on examples and comparative examples. It was confirmed by using conventional methods, such as electron microscopic photography or colorimetry that the surface of the powdery zinc oxide was coated with silicon oxide, etc., formed on the surface of the powdery zinc oxide.

(1) Photocatalytic activity evaluation (powder)

Evaluations were effected by using JEF-FE2XG manufactured by Nippon Electronics Co., Ltd. as ESR, 5,5-dimethyl-1-pyrroline-1-oxyd (DMPO) having the concentration of 1.5 wt % as a radical trapping agent and super oxide anion radicals targeted as radicals to be measured. Ultraviolet rays were irradiated at an irradiation energy of 20 mW/cm$^{-2}$ by using SPOT CURE-UIS25102 manufactured by Ushio Denki Co., Ltd. as an ultraviolet light source. The amount of the ultraviolet rays was measured by using Broad Band Power/Energy Meter 13PE001 manufactured by Griot Co., Ltd. The evaluations were effected by the above-mentioned radical-generating intensity angles. The larger the angle, the greater is the amount of radicals generated. On the other hand, the smaller the angle, the smaller the radicals generated, so that the photocatalytic activity is suppressed.

(2) Aggregated or not

Whether the powder was aggregated or not was judged by an expert inspector. The judgement was made from grittiness felt when the powder was applied to an inner portion of an arm.

(3) Crystalline analysis evaluation

The crystallinity was examined based on the half-value width in the use of the X-ray diffraction method according to the above definition. With respect to the non-coated and non-fired powdery raw zinc oxides, "O" is a case which satisfied the following relationship between the crystallinity and the half-value width of them, "X" a case which does not satisfy it.

If the crystallinity of the non-coated and non-fired powdery raw zinc oxides is not less than 0.7, the half-value width of each of the peaks of the (100) and (010) planes and those of the (101) and (011) planes after coating and firing fall in a range of 0.25±0.10, and each of the differences among the half-value widths of the peaks is not more than 0.02.

If the crystallinity of the non-coated and non-fired powdery raw zinc oxides is less than 0.7, the half-value width of each of the peaks of the (100) and (010) planes and those of the (101) and (011) planes after coating and firing fall in a range of 0.50±0.10, and each of the differences among the half-value widths of the peaks is not more than 0.02.

Measurement of the crystallinity of samples used in the present examples and the comparative examples according to the density method revealed that the samples having average primary particle diameters of not less than 0.3 μm exhibited a crystallinity of 0.7 or more, whereas the samples having average primary particle diameters of less than 0.3 μm exhibited the crystallinity of less than 0.7.

(4) Photocatalytic activity evaluation (Cosmetic preparations)

Evaluations were effected by the same powder evaluating method except that the concentration of the sample was changed to 0.1 wt %. The ratio of the radical-generating intensity angle in Example 14 to that in Comparative Example 17 was determined, and rounded off to obtain an evaluated result. In this evaluation, the smaller the value, the smaller the radical-generating amount, which shows that the photocatalytic activity is suppressed. An evaluation of Example 8 to Comparative Example 15 was also conducted.

(5) Functionality evaluation

Functionality of a sample (cosmetic preparation) was evaluated in a one-week continuous use test in the summer by using twenty expert panelists. Evaluation items were two: "whether the feel is excellent or not" and "whether sebum is felt floating or not. "Excellent feel and no sebum floating" was taken as "+5", and "bad feel and weak against sebum as "0", intermediate states being evaluated by four steps. Evaluation results were obtained by summing the marks of all the panelists. Therefore, the higher the mark, the better the evaluation.

(6) Ultraviolet light-shielding effect

The ultraviolet light-shielding effect of a sample (cosmetic preparation) was evaluated by using expert panelists. In the daytime, they played tennis, and ultraviolet light-shielding effect was evaluated based on sunburn (immediately blacked) state according to a evaluation standard given in Table 1. Therefore, the higher the mark, the better is the ultraviolet light-shielding effect.

TABLE 1

| State | Mark |
| --- | --- |
| Completely no instant blacking | + 5 points |
| Slight instant blacking recognized | + 2 points |
| Instant blacking recognized | 0 point |

Example 1

Into toluene were charged 88 parts by weight of finely powdery zinc oxide having the average primary particle diameter of 16 nm and 12 parts by weight of dimethyl polysiloxane (20 cSt, manufactured by Shinetsu Chemical Kogyo Co., Ltd.). After the mixture was well stirred, the toluene was removed by heating under a reduced pressure. The resulting powder was ground by using an atomizer. Then, the ground powder was fired at 800° C. for 2 hours in air by using a high temperature heating furnace, thereby obtaining a targeted reformed zinc oxide.

In this case, the firing treatment was such that after the sample was put into the light temperature furnace, the temperature was gradually raised from room temperature, and the sample was cooled in air after the intended firing condition was finished (This is the same as in the following).

Example 2

Into 95 parts by weight of finely powdered zinc oxide having an average primary particle diameter of 60 nm was charged, under stirring, 5 parts by weight of methyl hydrogen polysiloxane (KF-99P, manufactured by Shinetsu Chemical Kogyo Co., Ltd.) by using a sprayer. The mixture was preliminarily heated at 180° C. for 1 hour. Then, the resultant mixture was fired at 700° C. for 4 hours in air by using the high temperature heating furnace, thereby obtaining a targeted reformed zinc oxide.

Example 3

Into toluene were charged 95 parts by weight of finely powdery zinc oxide having the average primary particle diameter of 0.3 $\mu$m and 4 parts by weight of methyl hydrogen polysiloxane (KF-99P, manufactured by Shinetsu Chemical Kogyo Co., Ltd.). After the mixture was stirred well, the toluene was removed by heating under a reduced pressure. The resulting powder was ground by using the atomizer. Then, the ground powder was fired at 800° C. for 2 hours in air by using the high temperature heating furnace, thereby obtaining a targeted reformed zinc oxide.

Example 4

By using a ball mill, 87 parts by weight of finely powdered titanium oxide coated with zinc oxide and having an average primary particle diameter of 0.3 $\mu$m, 8 parts by weight of methyl hydrogen polysiloxane (KF-99P, manufactured by Shinetsu Chemical Kogyo Co., Ltd.) and finely powdered titanium oxide treated with silica-alumina and having an average primary particle diameter of 35 nm were mixed by using the ball mill. Then, the resulting powder was fired at 700° C. for 1 hour in air by using the light temperature heating furnace, thereby obtaining a targeted reformed zinc oxide-coated titanium oxide.

Example 5

Into 90 parts by weight of powdery zinc oxide having an average primary particle diameter of 10 $\mu$m and planar particle shapes was charged 10 parts by weight of methyl hydrogen polysiloxane (KF-9901, manufactured by Shinetsu Chemical Kogyo Co., Ltd.) by using a mixer. Then, the resultant mixture was fired at 850° C. for 1 hour in air by using the high temperature heating furnace, thereby obtaining a targeted reformed zinc oxide. Thereafter, the thus reformed zinc oxide planar-particles zinc were surface-treated with a perfluoroalkyl phosphoric acid triethanol amine liquid, thereby obtaining the reformed planar-particles treated with 5 wt % of fluorinated compound.

Example 6

60 parts by weight of powdery zinc oxide having an average primary particle diameter of 0.3 $\mu$m and 40 parts by weight of methyl hydrogen polysiloxane (KF-99P, manufactured by Shinetsu Chemical Kogyo Co., Ltd.) were charged into toluene. After the mixture was well stirred, the toluene was removed by heating under a reduced pressure. The resulting powder was ground by using the atomizer. Then, the ground powder was fired at 800° C. for 6 hours in air by using the high temperature heating furnace, thereby obtaining a targeted reformed zinc oxide.

Comparative Example 1

Powdery zinc oxide having an average primary particle diameter of 0.3 $\mu$m and tetrahydrogen tetramethylcyclotetrasiloxane were charged into different containers, respectively, which were kept in a desiccator at 80° C. for 16 hours. Then, a silicone layer was formed on the powdery zinc oxide in a gas phase. Thereafter, the resultant powder was heated at 500° C. for 4 hours in air by using the high temperature furnace, thereby obtaining a zinc oxide powder which was coated with silicon oxide by firing in the gas phase.

Comparative Example 2

Powdery zinc oxide having an average primary particle diameter of 0.3 $\mu$m and hexamethylcyclotrisiloxane were charged into different containers, respectively, which were kept in a desiccator at 80° C. for 16 hours. Then, a silicone layer was formed on the powdery zinc oxide in a gas phase. In this stage, the zinc oxide powder had water-repellant property. Thereafter, the resultant powder was heated at 500° C. for 4 hours in air by using the high temperature furnace, thereby obtaining a zinc oxide powder which was coated with silicon oxide by firing in the gas phase.

Comparative Example 3

Into 95 parts by weight of finely powdered zinc oxide having an average primary particle diameter of 60 nm was charged, under stirring, 5 parts by weight of methyl hydrogen polysiloxane (KF-99P, manufactured by Shinetsu Chemical Kogyo Co., Ltd.) by using a sprayer. Then, the mixture was fired at 1000° C. for 4 hours in air, thereby obtaining a reformed zinc oxide fine powder.

Comparative Example 4

Finely powdered zinc oxide having an average primary particle diameter of 16 nm was fired at 800° C. for 2 hours in air by using the high temperature heating furnace, thereby obtaining a reformed zinc oxide fine powder.

Comparative Example 5

Finely powdered zinc oxide having an average primary particle diameter of 60 nm was fired at 700° C. for 4 hours in air by using the high temperature heating furnace, thereby obtaining a reformed zinc oxide fine powder.

Comparative Example 6

Finely powdered zinc oxide having an average primary particle diameter of 0.3 μm was fired at 800° C. for 2 hours in air by using the high temperature heating furnace, thereby obtaining a reformed zinc oxide fine powder.

Comparative Example 7

Into toluene were charged 88 parts by weight of finely powdered zinc oxide having an average primary particle diameter of 16 nm and 12 parts by weight of dimethyl polysiloxane (20 cSt, manufactured by Shinetsu Chemical Kogyo Co., Ltd.). After the mixture was well stirred, the toluene was removed by heating under a reduced pressure. The resulting powder was ground by using the atomizer, thereby obtaining a reformed zinc oxide fine powder coated with silicone.

Comparative Example 8

Into 95 parts by weight of finely powdered zinc oxide having an average primary particle diameter of 60 nm was charged, under stirring, 5 parts by weight of methyl hydrogen polysiloxane (KF-99P, manufactured by Shinetsu Chemical Kogyo Co., Ltd.) by using a sprayer. Then, the mixture was fired at 180° C. for 1 hour in air, thereby obtaining a silicone-treated zinc oxide fine powder.

Comparative Example 9

A slurry was obtained by dispersing 92 parts by weight of finely powdered zinc oxide having an average primary particle diameter of 16 nm into 800 parts by weight of purified water. Then, 20 parts by weight of a 30 wt % aqueous solution of sodium silicate was added into the slurry, into which 20 parts by weight of a 10 wt % aqueous solution of aluminum chloride was slowly added under stirring. Then, a 1 N aqueous solution of hydrochloric acid was added into the mixture dropwise, thereby adjusting its pH to 6.5. The obtained solution was filtered, and the powder was dried at 120° C. for 12 hours. The dried powder was ground by using the mixer, thereby obtaining a zinc oxide fine powder coated with silicon oxide and aluminum oxide precipitated due to pH change.

Comparative Example 10

A slurry was obtained by dispersing 85 parts by weight of finely powdered zinc oxide having an average primary particle diameter of 16 nm into 800 parts by weight of purified water. Then, 15 parts by weight of sodium stearate was added dropwise into the slurry under stirring. Then, a 1 N aqueous solution of hydrochloric acid was added into the mixture, thereby adjusting its pH to 6.8. The obtained solution was filtered, and the powder was dried at 120° C. for 12 hours. The dried powder was ground by using the mixer, thereby obtaining a zinc oxide fine powder coated with a metallic soap (zinc stearate).

Comparative Example 11

By using the mixer, 98 parts by weight of finely powdered zinc oxide having an average primary particle diameter of 16 nm and 2 parts by weight of dimethyl polysiloxane (20 cSt, manufactured by Shinetsu Chemical Kogyo Co., Ltd.) were mixed well, and the mixture was ground by using the atomizer. Then, the resultant mixture was fired at 500° C. for 1 hour in air by using the high temperature heating furnace, thereby obtaining the treated zinc oxide.

Comparative Example 12

Into isopropyl alcohol were charged 95 parts by weight of powdery zinc oxide having an average primary particle diameter of 0.3 μm, 3 parts by weight of trimethyl ethoxysilane, and 2 parts by weight of an aluminum coupling agent. After the mixture was stirred well, the solvent was removed. Then, the ground powder was fired at 600° C. for 2 hours in air by using the high temperature heating furnace, thereby a zinc oxide powder coated with silicon oxide and aluminum oxide was obtained.

Comparative Example 13

Into isopropyl alcohol were charged 97 parts by weight of powdery zinc oxide having an average primary particle diameter of 10 μm with planar particle shapes and 3 parts by weight of trimethyl ethoxysilane. After the mixture was stirred well, the solvent was removed, the powder was fired at 600° C for 2 hours in air by using the high temperature heating furnace, thereby a zinc oxide powder coated with silicon oxide.

Example 7

A sun screening agent was obtained according to the recipe given below.

TABLE 2

| Compounded ingredient | Compounded amount (%) |
|---|---|
| Component A | |
| Modified zinc oxide fine power (Example 2) | 12 |
| Inorganic ultraviolet light-shielding ingredient Alumina/silica-treated titanium oxide fine powder (average primary particle diameter 35 nm)) | 5 |
| Silicone resin beads | 2 |
| Octamethyl cyclopentasiloxane | 30 |
| Trimethylsiloxysilicate | 3 |
| Polyethermodified silicone | 3 |
| Organic ultraviolet light-absorber (Parsol MCX) | 10 |
| Component B | |
| Ethanol | 6 |
| Antiseptics | appropriate amount |
| Antioxidant (vitamin C) | 0.1 |
| Purified water | remainder |

The components A were roughly mixed, and then ground by using a ball mill. While the obtained slurry was being stirred, the components B, which were uniformly dissolved, were added to the mixture, followed by sufficient stirring. After the resulting mixture was packed into a container together with stirring balls, thereby obtaining a product. The product was used after shaking it before use.

Comparative Example 14

A sun screen agent was obtained in the entirely same manner as in Example 7 except that non-treated powdery zinc oxide (the same average primary particle diameter of 60 nm as used in Example 2) was used instead of the reformed finely powdered zinc oxide powder (Example 2) in Example 7.

Example 8

A foundation was obtained according to a recipe given below. As a fluorinated compound-treating pigment, a fluorinated compound-treating pigment treated with a perfluoroalkyl phosphoric acid ester salt at 5 wt % was used. Further, as a silicone elastomer/dimethyl polysiloxane kneaded mixture, a silicone elastomer having a concentration of 40 wt % was used. As the silicone elastomer, Trefil E (−507 grade) (manufactured by TORAY DOW CORNING SILICONE CO., LTD.) was used. The unit is "wt %". As the antioxidant, a tea extract obtained by dry distilling and solvent-extracting tea leaves and containing polyphenol, etc., was used.

TABLE 3

| Compounded ingredient | Amount (%) |
|---|---|
| Component A | |
| Modified zinc oxide fine power (Example 2) | 5 |
| Fluorinated compound-treated (Example 5) | 30 |
| Inorganic ultraviolet light-shielding ingredient | 5 |
| fluorinated compound-treated alumina/silica-treated titanium oxide fine powder | |
| (average primary particle diameter 35 nm) | |
| fluorinated compound-treated titanium oxide | 8 |
| (average primary particle diameter 0.23 µm) | |
| Fluorinated compound-treated iron oxide | 4.5 |
| Fluorinated compound-treated cericite | 10 |
| Fluorinated compound-treated talc | 20 |
| Component B | |
| Silicone elastomer/dimethylpolysiloxane kneaded mixtures | 10 |
| Perfluoroalkyl-polyoxyalkylene-comodified silicone (HLB = 1.1) | 3 |
| Organic ultraviolet light-absorber (Parsol MCX) | 3 |
| Glycerol | 0.4 |
| Isononyl isononanoate | 0.5 |
| Antioxidant (tea extract, calculated as evaporation residue) | 0.1 |
| Antiseptics | appropriate amount |

Each of components A and B were mixed by using a mixer. While the mixed components A were being stirred, the mixed components B were added dropwise slowly to the components B. After the mixture was further well mixed with the mixer, the mixture was ground by using an atomizer, which was molded in a metal dish as a foundation by using a mold.

Comparative Example 15

A foundation was obtained in the entirely same manner as in Example 8 except that a non-treated, finely powdered zinc oxide (the same as used in Example 2) was used instead of the reformed zinc oxide fine powder (Example 2), and that the non-treated zinc having planar particle shapes (the same as used in Example 5) was used instead of the fluorine-treated reformed zinc oxide having the planar particle shapes (Example 5).

Comparative Example 16

A foundation was obtained in the entirely same manner as in Example 8 except that the silicon oxide/aluminum oxide-coated zinc oxide obtained in Comparative Example 12 was used instead of the reformed zinc oxide fine powder in Example 8 (Example 2), and that the silicon oxide-coated, planar-particle zinc oxide obtained in Comparative Example 13 was used instead of the fluorine-treated reformed zinc oxide having the planar particle shapes (Example 5).

In the following, evaluation results of the modified zinc oxides in the above Examples and Comparative Examples are given in Table 4.

TABLE 4

|  | Photocatalytic activity | Aggregation | Analysis on crystalline structure |
|---|---|---|---|
| Example 1 | 0 | no | ○ |
| Example 2 | 0 | no | ○ |
| Example 3 | 0 | no | ○ |
| Example 4 | 0 | no | ○ |
| Example 5 | 0 | no | ○ |
| Example 6 | 0 | no | ○ |
| Comparative Example 1 | 0 | present | x |
| Comparative Example 2 | 6 | present | x |
| Comparative Example 3 | 1 | slightly present | x |
| Comparative Example 4 | 9 | present | x |
| Comparative Example 5 | 2 | present | x |
| Comparative Example 6 | 8 | present | x |
| Comparative Example 7 | 13 | no | x |
| Comparative Example 8 | 12 | no | x |
| Comparative Example 9 | 6 | present | x |
| Comparative Example 10 | 6 | present | x |
| Comparative Example 11 | 7 | no | x |
| Comparative Example 12 | 8 | present | x |
| Comparative Example 13 | 5 | present | x |

It is seen from Table 4 that the zinc oxide treated in each of the Examples of the present invention has a suppressed photocatalytic activity and crystalline structure in the specified range.

In contrast thereto, it is seen that each of the Comparative Examples is inferior with respect to any of the performances. In Comparative Example 7 in which the zinc oxide was merely coated with dimethyl polysiloxane, neither of the effects aimed at by the present invention is not attained. In Comparative Example 8 in which the product was coated with methyl hydrogen polysiloxane, conventionally used, and heated at a low temperature, it is seen that the photocatalytic activity-suppressing effect was recognized. In Comparative Example 9 regarding the product wet-coated with silicon oxide and aluminum oxide, the feel was deteriorated due to vigorous aggregation, although the photocatalytic activity was suppressed. In Comparative Example 10 regarding the metallic soap treated by the wet method, its performances were not enough. In Comparative Example 1 in which the tetrahydrogen tetramethyl cyclotetrasiloxane as the volatile polysiloxane compound was reacted in the gas phase state, the powder was strongly aggregated, although the photocatalytic activity was suppressed after the firing. In Comparative Example 2 in which the hexamethyl cyclotrisiloxane as a volatile compound as in Comparative Example 1, was reacted in the gas phase state, followed by the firing step, the photocatalytic activity was not sufficiently suppressed, and the powder was strongly aggregated. In Comparative Example 11 in which the treating temperature was low, it is seen that the photocatalytic activity was not sufficiently suppressed.

Further, in each of Comparative Example 12 in which the zinc oxide was coated with silicon oxide and aluminum oxide by using the silane compound and the aluminum coupling agent and Comparative Example 13 in which the zinc oxide was coated with silicon oxide by using the silane compound, the photocatalytic activity was not sufficiently suppressed and the powder was also aggregated.

As those which were judged to fall outside the range, some had the half-value widths falling outside the specified range, and other had the difference in the half-value widths between the (100) and (101) planes and the (101) plane and (011) planes exceeding the specified range.

With respect to the above Examples 1 to 3 and Comparative Examples 1 to 6, the crystalline structure analysis results of the powders are summarized in Table 5. In Comparative Examples 4 to 6, the heat treatment was effected under the corresponding firing temperature condition without using the surface active agent in any of Examples 1 to 3. It is seen from Table 5 that each of the Examples of the present invention has a crystalline structure falling in the specified range.

TABLE 5

|  | Crystallinity of powdery zinc oxide as raw material | Half-value width | | Absolute value of half-value width | Judgement on crystalline structure analysis |
| --- | --- | --- | --- | --- | --- |
|  |  | (100)(010) phase | (101)(011) phase |  |  |
| Example 1 | 35.5 | 0.520 | 0.525 | 0.005 | ○ |
| Example 2 | 19.4 | 0.505 | 0.495 | 0.010 | ○ |
| Example 3 | 99.8 | 0.240 | 0.235 | 0.005 | ○ |
| Comparative Example 1 | 99.8 | 0.265 | 0.175 | 0.090 | x |
| Comparative Example 2 | 99.8 | 0.245 | 0.185 | 0.060 | x |
| Comparative Example 3 | 19.4 | 0.235 | 0.200 | 0.035 | x |
| Comparative Example 4 | 35.5 | 0.195 | 0.145 | 0.050 | x |
| Comparative Example 5 | 19.4 | 0.175 | 0.155 | 0.020 | x |
| Comparative Example 6 | 99.8 | 0.140 | 0.140 | 0.000 | x |

Next, the evaluation result of each of the cosmetic preparations produced in the above Examples and Comparative Examples are given in Tables 6 and 7.

TABLE 6

|  | Photocatalytic activity |
| --- | --- |
| Example 7 | 0 |
| Example 8 | 10 |

TABLE 7

|  | Feel | Sebum resistance | Ultraviolet light-shielding effect |
| --- | --- | --- | --- |
| Example 7 | 86 | 80 | 30 |
| Comparative Example 14 | 64 | 70 | 30 |
| Example 8 | 92 | 86 | 30 |
| Comparative Example 15 | 66 | 64 | 30 |
| Comparative Example 16 | 60 | 60 | 30 |

It is seen from Table 6 that the cosmetic preparation in each of Examples of the present invention has a photocatalytic activity more suppressed as a product as compared with the Comparative Examples. This shows that the deterioration of the products can be more suppressed in the case that they are stored or used.

Further, it is seen that as compared with the Comparative Examples, the cosmetic preparation in each of the Examples of the present invention has a more excellent feel, smaller sebum floating with more excellent sebum resistance, and that the ultraviolet light-shielding power was not deteriorated despite of the surface-coating.

Industrially applicability

From the above, when the powdery zinc oxide is coated with the silicone compound in the non-gaseous phase and then is fired in a temperature range of 600 to 950° C., an activity-suppressed zinc oxide powder having the suppressed photocatalytic activity and excellent feel is obtained, and the cosmetic preparations in which the activity-suppressed zinc oxide powder is incorporated have excellent product stability, feel, sebum resistance and ultraviolet light-shielding effects.

What is claimed is:

1. An activity-suppressed zinc oxide powder coated with silicon oxide, said activity-suppressed zinc oxide powder being obtained by coating powdery zinc oxide with at least one silicone compound selected from the group consisting of an organo polysiloxane and a silicone resin in a non-gaseous phase to form a resulting powder, and firing the resulting powder at a temperature of 600 to 950° C. in an oxygen-containing atmosphere.

2. The activity-suppressed zinc oxide powder set forth in claim 1, wherein the powdery zinc oxide has an average primary particle diameter of 5 nm to 20 μm.

3. The activity-suppressed zinc oxide powder set forth in claim 1, wherein the powdery zinc oxide has an average primary particle diameter of 10 nm to 300 μm.

4. The activity-suppressed zinc oxide powder set forth in claim 1, wherein the amount of the silicone compound covering the powdery zinc oxide is 2 to 80 wt. % of the total weight of the powdery zinc oxide and the silicone compound.

5. The activity-suppressed zinc oxide powder set forth in claim 4, wherein the covering amount of the silicone compound is 2 to 9 wt. %.

6. The activity-suppressed zinc oxide powder set forth in claim 1, wherein said powder has generation intensity angles of super oxide anion radicals immediately after commencement of light irradiation of not more than 4 degrees.

7. A cosmetic preparation containing an activity-suppressed zinc oxide powder coated with silicon oxide, said activity-suppressed zinc oxide powder being obtained by coating powdery zinc oxide with at least one silicone compound selected from an organo polysiloxane and a silicone resin in a non-gaseous phase to form a resulting powder, and firing the resulting powder in an oxygen-containing atmosphere.

8. The cosmetic preparation set forth in claim 7, which further comprises at least one ultraviolet light-shielding ingredient.

9. The cosmetic preparation set forth in claim 7, wherein at least one antioxidant is further compounded.

10. A method of producing an activity-suppressed zinc oxide powder coated with silicon oxide comprising the steps of coating zinc oxide powder with at least one silicone compound in a non-gaseous phase and selected from the group consisting of an organo-polysiloxane and a silicone resin to form a resulting powder and firing the resulting powder at a temperature of 600 to 950° C. in an oxygen-containing atmosphere to form the activity-suppressed zinc oxide powder.

11. The method of claim 10, wherein the zinc oxide powder has an average primary particle diameter of 5 nm to 20 $\mu$m.

12. The method of claim 10, wherein the zinc oxide powder has an average primary particle diameter of 10 nm to 300 $\mu$m.

13. The method of claim 10, wherein the amount of the silicone compound coating the zinc oxide powder is 2 to 80 wt. % of the total weight of the coated zinc oxide particles.

14. The method of claim 13, wherein the amount of the silicone compound coating the zinc oxide powder is 2 to 9 wt. %.

* * * * *